United States Patent [19]

LeMay et al.

[11] 4,101,773
[45] Jul. 18, 1978

[54] RADIOGRAPHY

[75] Inventors: Christopher Archibald Gordon LeMay, Osterley; Robert Paul Randall, Uxbridge, both of England

[73] Assignee: EMI Limited, Hayes, England

[21] Appl. No.: 735,012

[22] Filed: Oct. 26, 1976

[30] Foreign Application Priority Data

Nov. 4, 1975 [GB] United Kingdom ............... 45726/75

[51] Int. Cl.² .......................................... H05G 1/26
[52] U.S. Cl. .................................... 250/401; 250/355
[58] Field of Search ..................... 250/354, 355, 401

[56] References Cited

U.S. PATENT DOCUMENTS 3,345,516  10/1967  Nicholson et al. ............... 250/355
3,949,229  4/1976  Albert ............................. 250/401

Primary Examiner—Davis L. Willis
Attorney, Agent, or Firm—Cooper, Dunham, Clark, Griffin & Moran

[57] ABSTRACT

Radiographic apparatus is described in which an X-ray tube incorporates a cathode which is heavily driven to produce a strong electron beam. In order to minimize the demands placed on the cathode, the X-radiation emitted by the tube (or the electron beam produced by the cathode and causing the emission of the X-radiation) is monitored and used to control the supply of energy (e.g. heater current) to the cathode.

7 Claims, 3 Drawing Figures

RADIOGRAPHY

The present invention relates to radiography and it relates especially, although not exclusively, to that branch of radiography known as computerised axial tomography.

In certain kinds of computerised axial tomographic apparatus it is necessary, in order to generate suitable quantities of X-radiation, to operate an X-ray generating tube with a heavy electron beam current. Particularly when it is required that the X-rays be emitted from a small spot or from a fine line on the anode of the tube, it is necessary to utilise a small cathode which is operated at a high temperature in order to cause it to emit sufficient electrons to provide the heavy electron beam current which is required. This causes the heater, which is usually the cathode itself, to have a limited life.

It is an object of this invention to provide radiographic apparatus in which the problem described in the preceding paragraph is reduced.

According to the invention there is provided radiographic apparatus including and X-ray tube having a cathode, means for supplying said cathode with energy to cause it to emit electrons, an anode arrangement incorporating an X-ray emissive target, means constraining said electrons emitted from said cathode form a beam directed towards said target, and means for regulating said supply of energy to said cathode in dependence upon the strength of said electron beam.

In order that the invention may be clearly understood and readily carried into effect, one embodiment thereof will now be described, by way of example only, with reference to the accompanying drawings.

Figure 1:
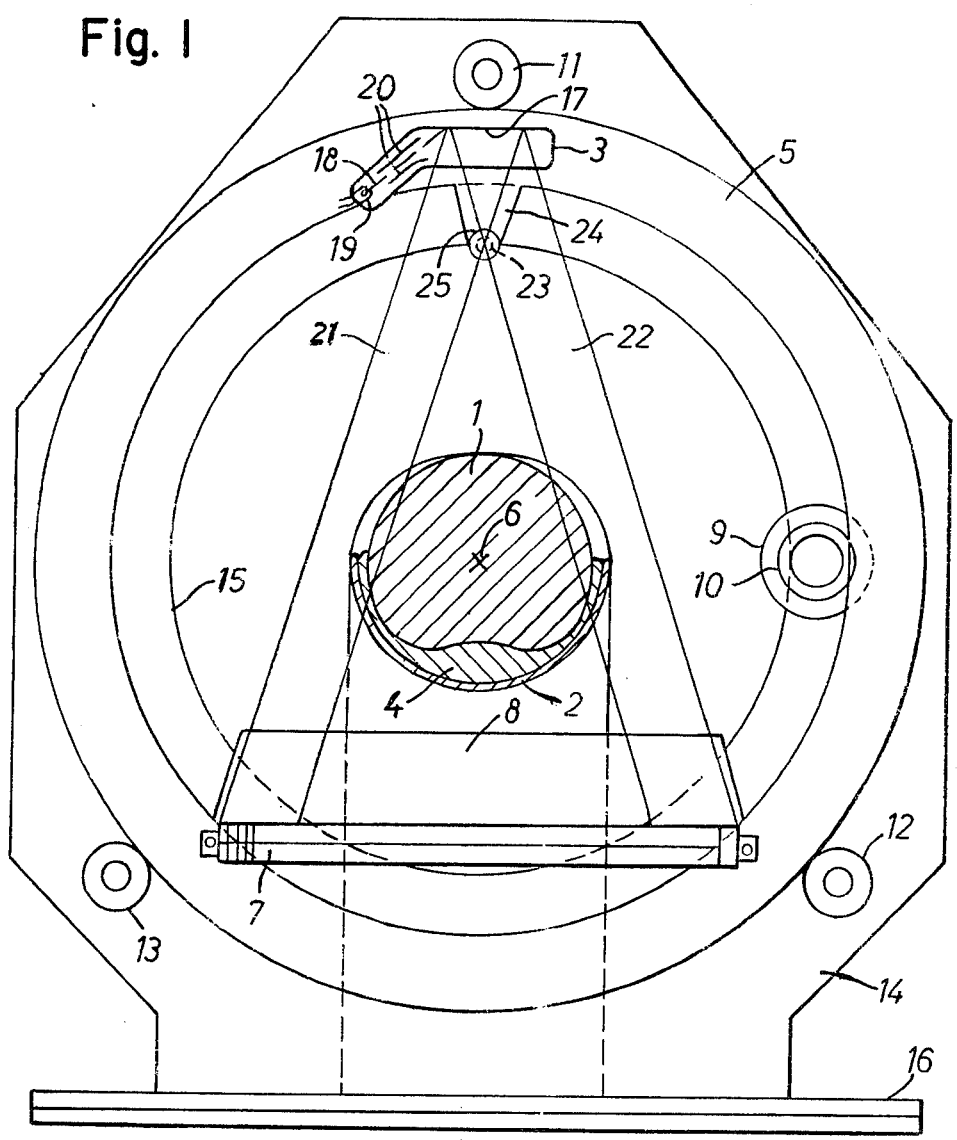
FIG. 1 shows, in front elevational view, radiographic apparatus in accordance with one example of the invention.
Figure 1A:
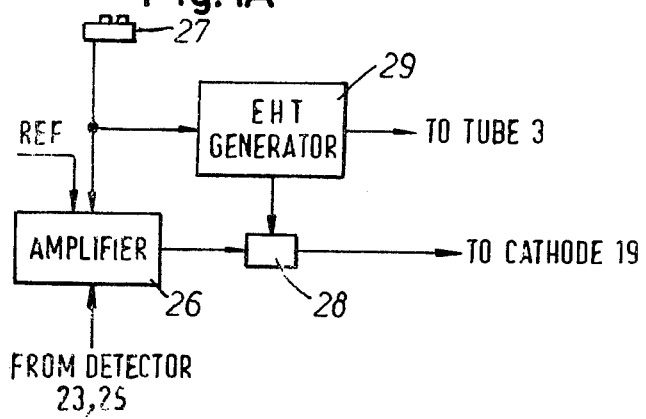
FIG. 1a shows in block form a circuit used in the apparatus of FIG. 1.

Referring now to the drawing, a body 1 to be examined is supported supine on a curved bed 2. A source 3 of penetrating radiation, in this example X-radiation, is arranged to generate a planar sweep of the radiation, and the body 1 is positioned so that the plane of the sweep of radiation coincides with a slice through the body 1 which is to be investigated. Packing material 4 is disposed between the body 1 and the bed 2 so as to fill gaps therebetween; the material 4 being preferably of dough-like consistency and absorbing X-radiation to an extent similar to the body 1. Material 4 is preferably contained in one or more plastic bags.

The source 3 is mounted on a rotatable ring member 5, which can rotate about an axis 6 which passes through the body 1 perpendicularly to the plane of the sweep of radiation, so that the radiation can be projected through the slice of the body 1 from a plurality of different directions. The ring member 5 also carries an array 7 of detectors, each of which views the source throught a respective collimator, the collimators being disposed in a bank 8.

Ring member 5 and its attachments are rotated about the axis 6 by means of a motor 9 which drives a gear wheel 10, the latter being arranged to co-operate with gear teeth cut into the inner periphery of the ring member 5. The ring member 5 is supported by, and rotates within, three roller bearings 11, 12 and 13 which, like the motor 9 and gear wheel 10, are secured to a main frame memeber 14. The frame member 14 is formed with an aperture 15 which is concentric with the ring member 5, and said member 14 is secured to a pedestal 16 which is fixed to the floor of a building. It will be appreciated that the main frame 14 remains fixed, whilst the ring member 5 and its attachments can rotate relative thereto.

It will be observed that the source 3 comprises an X-ray tube which contains an elongated anode 17 over which the electron beam 18 emitted from a cathode 19 can be scanned by means of deflection plates 20. Electromagnetic deflection coils could, of course, be used instead of the plates 20. In either event, however, the array 7 of detectors remains fixed on the ring member 5 since it has sufficient breadth to accomodate the scanning of the source.

In operation of the apparatus, the ring member 5 and its attachments are rotated about the axis 6 and the electron beam 18 is scanned across the target 17 in synchronism therewith but at a substantially faster cycling rate so that for each incremental angle of rotation of the member 5 the electron beam is scanned across the target 17 from left to right and then rapidly flies back, thus scanning the X-radiation from the position shown at 21 in the drawing to a position similar to that shown at 22 (bearing in mind that, by this time, an increment of rotation will have occurred). The scanning and the reasons therefor are described in considerable detail in U.S. application Ser. No. 630779 and British Application No. 43984/75 to which the Reader's attention is respectfully directed and thus will not be further described herein. Suffice to say that the end result of the scanning is to derive, from the detectors of array 7, output signals indicative of the absorption suffered by the radiation from source 3 on traversing a plurality of sets of paths through the body 1. The paths of a set are substantially parallel to one another, and each set of paths is disposed at a respective angular orientation with respect to the body 1 and in the plane of the slice.

The output signals so produced are processed by any suitable technique for example the one described and claimed in U.S. Pat. No. 3,924,129 to permit the evaluation of the absorption coefficient, with respect to the radiation from the source 3 at each of a plurality of locations distributed over the aforementioned slice of the body.

The cathode 19 is typically formed of a flat tape of foil; the surface finish of the tape or foil being sufficiently smooth, as described in British Application No. 42865/75 etc. (cognate) to produce a ribbon-like electron beam 18 of high current density which is accurately focussed on the anode 17. When the cathode is operated at a sufficiently high temperature to emit the required quantities of electrons, material can evaporate from the cathode, thus weakening it and eventually causing its destruction. In accordance with one aspect of this invention, the cathode temperature is controlled, whilst at the aforementioned high temperature, so that it emits only the required amount of electrons.

In order to effect said aspect of the invention, a further radiation detector 23 is mounted by means of a bracket 24 secured to the front surface of the ring member 5 so that it lies between the source 3 and the body 1 in a position where it will always intercept some radiation, irrespective of the point incidence of beam 18 on anode 17, provided, of course, that the tube 3 is operational. The detector 23 conveniently comprises a scintillator cystal and is optically coupled to a photomultiplier tube 25 which is also mounted on the bracket 24 and is disposed with its axis perpendicular to the plane of the sweep of radiation (i.e. parallel to the axis 6). Electrical output signals indicative of the strength of X-radiation incident on the detector 23 are fed from the tube 25 to an amplifier circuit 26. The amplifier circuit 26 is also supplied with START and STOP signals from a remotely located hand set 27, and with a reference voltage. Output signals from amplifier 26 are fed by way of a switch unit 28, operated in response to the condition of an E.H.T. generator 29 which provides the E.H.T. for the source 3, to the cathode 19 of the source 3 and constitute the heating current therefor.

In operation, when it is desired to energise the X-ray source 3, a START signal is supplied to the amplifier 26 from the hand set 27. This causes (in a manner which will be fully described hereinafter) an initial heating current of about ten amps to flow through the cathode 19 provided that the E.H.T. generator 29 is operative. If this unit has failed, the switch unit 28 is caused to assume an open circuit condition, thereby preventing damage to the cathode which could occur if the heating current were applied thereto in the absence of E.H.T. being applied to the source tube 3. Once the cathode 19 has reached its operating temperature and X-radiation is being generated, this is detected by the detector 23 and a signal indicative of the strength of the X-radiation emitted from the source 3 is developed in the photomultiplier tube 25. This signal is applied to the amplifier 26 where it is compared with the reference voltage, the effects of the START command signal having terminated. The difference between the signal developed in tube 25 and the reference signal is applied to the output stage of the amplifier 26, this stage comprising a single transistor operated in Class A mode and arranged to provide no output when the strength of the X-radiation, as monitored by the detector 23, exceeds the required strength (as represented by the reference voltage) and to provide a substantial heating current to the cathode 19 when the strength of the X-radiation is substantially less than the required level. Between these limits, the amplifier characteristic is linear and permits a stable operating condition to be established. The average current supplied to the cathode 19 during an examination period is about four amps and it will be appreciated that the servo action provided by the arrangement described above is effective to vary the heating current so as to maintain the strength of the X-radiation at a value set by the reference voltage applied to the amplifier 26.

This voltage is switched to a negative value in response to the application to said amplifier 26 of the STOP command pulse. This means that the signal derived from detector 23 always exceeds the reference value and the heating current to the cathode 19 is discontinued. This condition prevails even when the source 3 is no longer producing X-radiation, since the output signal derived from detector 23 cannot fall below zero and thus the heating current remains cut-off. When it is desired to render the source 3 operative again, the START signal is applied to the amplifier 26. This is effective to raise the reference voltage to a substantial, positive value thereby causing it to exceed the signal applied to the amplifier 26 from the tube 25 (which is initially zero) by a sufficient extent to cause the aforementioned initial heating current of ten amps to be supplied to the cathode 19. Once the cathode has reached its operating temperature, the amplitude of the reference voltage is decreased to a level consistent with the minimum strength of X-radiation required from the source 3 and the servoing action is operative to cause the emission of said radiation to be maintained at said minimum level.

In an alternative mode of operation a reference voltage, dimensioned to balance a zero signal from the detector 23, 25 when the tube 3 is not operating, is applied to the amplifier 26. When the tube is to be rendered operative, the hand set 27 is used to apply a different reference signal (through a suitable gate which is not shown) which causes the correct X-radiation output to occur. Removal of this signal re-instates the original reference voltage thus causing X-radiation emission to cease.

It is a characteristic of cathodes of the kind described that there is only a small difference in temperature between a state in which the cathode has a long life expectancy and the state, at a somewhat elevated temperature, at which the required high electron emission is obtained, in which the cathode can be rapidly destroyed. Thus, instead of turning the heating current for the cathode completely off during periods when the source 3 is not required to generate X-radiation, the heating current can be merely reduced to a level consistent with maintaining the cathode in the first mentioned state. This can be effected by suitable adjustment of the reference voltage applied to the amplifier 26 during the various phases of operation of the source 3.

Figure 2:
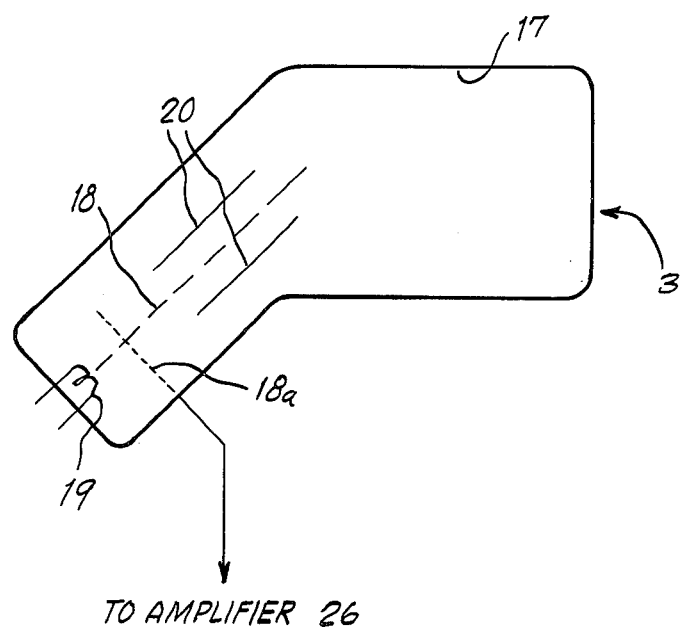
FIG. 2 shows part of a radiographic apparatus in accordance with another example of the invention.

As a further alternative, instead of using a detector/photomultiplier combination such as 23, 25 to detect the radiation emitted from the source 3 so as to provide the servoing information, the strength of the electron beam 18 can be monitored, for example by extracting a portion of the electron beam current by means of a grid or similar electrode in the source tube. Such an alternative arrangement is shown schematically in FIG. 2, where the grid or similar electrode is designated 18a. It will be appreciated that, since the anode 17 is the only intermediary between the electron beam 18 and the beam of X-radiation emitted from the source 3, there will be a strong correlation between the strengths of the two beams.

It will be appreciated that, since the source 3 is mounted on the ring member 5, the plane in which the radiation is emitted is above the plane of the front surface of the ring member. Thus the detector array 7, the bank of collimators 8, the detector 23 and the photomultiplier 25 stand above the plane of the front surface or ring member 5, being mounted thereto by respective brackets which are constructed so as to avoid fouling the gear wheel 10 during rotation. The gear wheel 10 does not protrude above the plane of the front surface of ring member 5.

In accordance with another arrangement, the initial heating of the cathode is limited to a predetermined amount by storing the appropriate amount of electrical energy in a capacitor and discharging the capacitor through the cathode, or through a transformer winding closely coupled to the cathode, in response to the receipt of the aforementioned START command. This technique avoids the necessity for an interlock with the E.H.T. circuit to be provided in respect of the initial heating current, since the cathode will only be supplied with a predetermined amount of power, and if the E.H.T. generator 29 fails then the tube will merely fail to operate. The amplifier 26 is, in this case, arranged to be incapable of supplying more than, say, five amps to the cathode 19. The amplifier 26 is still coupled to the cathode via the switch device 28, but in this case the said device 28 has only to be capable of switching (say) five amps as opposed to the ten amps which it is required to pass in the embodiment first described.

It will be appreciated that the apparatus can take other forms than that shown in FIG. 1 without departing from the scope of the invention. For example attenuating material may be disposed between the source 3 and the body 1 and/or between the body 1 and the collimator bank 8 to tend to reduce the differences in absorption which would otherwise be suffered by the radiation on traversing paths of substantially different lengths through the body 1. Moreover the source 3 need not be of the kind shown. It could for instance comprise a conventional X-ray tube and constitute a source of a single, pencil-like beam or a fan shaped spread of radiation, the source in either case being physically scanned laterally across the body in the plane of interest as well as being orbited around the body 1. As a further alternative, the source might be arranged to produce a fan shaped spread of radiation of sufficient angular extent to embrace the whole of the body 1 in the plane of the spread. In such a case, of course, the scanning need only comprise rotational movement.

Finally, since at least some of the detectors in the array 7 have to view the source point through a collimator which is of more than sufficient width to admit radiation travelling along a single path (in order to accommodate the scanning movement of the electron beam across the anode 17) it has been discovered that scattered radiation can present difficulties. If the ring member 5 is rotated through 360°, and the output signals relating to beam paths which are identical, but traversed from two opposite directions, are added and averaged, the effects of scatter can be substantially reduced.

What we claim is:

1. Radiographic apparatus including an X-ray tube arrangement having an electron emissive cathode, means for supplying energy to said cathode, during operation of said tube, to cause said cathode to emit electrons, means constraining said electrons to form a beam, an X-ray emissive target disposed to intercept said beam and adapted to emit X-radiation in response to the impingement thereon of said beam, support means supporting said tube, in spaced relationship with respect to a patient, so that said radiation travels towards the patient, detector means, disposed in the space between said tube and the patient, to detect radiation emitted by said tube, said detector means producing an output signal indicative of the amount of said radiation detected thereby, and regulating means utilising said output signal to regulate the supply of energy to said cathode, thus controlling the amount of X-radiation emitted by said tube.

2. Apparatus according to claim 1 wherein said means for supplying energy comprises a supply of heating current for said cathode.

3. Apparatus according to claim 1 including means for providing a reference signal, and means for comparing said output signal with said reference signal and for controlling said supply of energy to said cathode by said supplying means in dependence upon the result of said comparing.

4. Apparatus according to claim 3 wherein said regulating means includes an amplifier operated in Class A mode and arranged to regulate said supply of energy in direct dependence upon the result of said comparing.

5. Apparatus according to claim 3 including means for selectively supplying said regulating means with a starting signal which exceeds said output signal by a substantial amount to thereby cause said regulating means to supply, in response to said starting signal, an amount of energy to said cathode to initiate an emission of electrons sufficient to cause said target to emit said X-radiation.

6. Apparatus according to claim 5 including means for selectively supplying said regulating means with a termination signal which is exceeded to a substantial extent by said output signal to thereby cause the regulating means to cut off, in response to said termination signal, said supply of energy to said cathode.

7. Radiographic apparatus including an X-ray tube arrangement having an electron emissive cathode, means for supplying energy to said cathode, during operation of said tube, to cause said cathode to emit electrons, means constraining said electrons to form a beam, an X-ray emissive target disposed to intercept said beam and adapted to emited X-radiation in response to the impingement thereon of said beam, monitoring means for monitoring the strength of said electron beam and for developing an electrical output signal indicative of the strength of said beam, and regulating means utilising said output signal to regulate the supply of energy to said cathode, thus controlling the amount of X-radiation emitted by said tube.

* * * * *